United States Patent
Rosen et al.

(10) Patent No.: US 6,984,749 B2
(45) Date of Patent: Jan. 10, 2006

(54) METHOD FOR INHIBITING POLYMERIZATION DURING THE RECOVERY AND PURIFICATION OF UNSATURATED MONONITRILES

(75) Inventors: Bruce I. Rosen, Park Ridge, IL (US); Bruce E. Firth, Buffalo Grove, IL (US)

(73) Assignee: BP Corporation North America Inc., Warrenville, IL (US)

( * ) Notice: Subject to any disclaimer, the term of this patent is extended or adjusted under 35 U.S.C. 154(b) by 514 days.

(21) Appl. No.: 10/309,962

(22) Filed: Dec. 4, 2002

(65) Prior Publication Data

US 2004/0110977 A1 Jun. 10, 2004

(51) Int. Cl.
*C07C 255/03* (2006.01)

(52) U.S. Cl. ........................................ 558/306; 558/466
(58) Field of Classification Search ................ 558/306, 558/466
See application file for complete search history.

(56) References Cited

U.S. PATENT DOCUMENTS

| | | | |
|---|---|---|---|
| 3,691,226 A | 9/1972 | Halvorson et al. | 260/465.9 |
| 4,720,566 A | 1/1988 | Martin | 558/306 |
| 5,396,004 A | 3/1995 | Arhancet et al. | 585/5 |
| 5,396,005 A | 3/1995 | Arhancet | 585/5 |
| 5,416,258 A | 5/1995 | Arhancet et al. | 585/3 |
| 5,426,257 A | 6/1995 | Arhancet | 585/5 |
| 5,446,220 A | 8/1995 | Arhancet | 585/5 |
| 5,489,718 A | 2/1996 | Arhancet | 585/5 |
| 5,489,720 A | 2/1996 | Arhancet | 585/5 |
| 5,510,547 A | 4/1996 | Arhancet et al. | 585/5 |
| 5,648,574 A | 7/1997 | Arhancet et al. | 585/5 |
| 5,869,730 A | 2/1999 | Graham et al. | 585/320 |
| 5,895,822 A | 4/1999 | Monical et al. | 558/320 |
| 6,084,121 A * | 7/2000 | Rogers et al. | 558/466 |
| 6,238,574 B1 | 5/2001 | Cesa et al. | 210/763 |
| 6,262,323 B1 | 7/2001 | Elder | 585/5 |
| 6,403,850 B1 | 6/2002 | Benage et al. | 585/5 |
| 6,627,766 B2 * | 9/2003 | Reid et al. | 558/305 |

* cited by examiner

*Primary Examiner*—Cecilia Tsang
*Assistant Examiner*—Ebenezer Sackey
(74) *Attorney, Agent, or Firm*—Fred S. Jerome; Thomas E. Nemo

(57) ABSTRACT

Economical processes are disclosed for recovery and refining of valuable nitrogen-containing organic compounds formed by catalytic oxidation of least one feed compound selected from the group consisting of propane, propylene, isobutane and isobutylene in the presence of ammonia to produce a gaseous. Processes of the invention include quenching the gaseous reactor effluent with an aqueous quench liquid; forming an aqueous solution comprising the corresponding unsaturated mononitrile, hydrogen cyanide and other organic co-products; and using an integrated sequence of distillations and phase separations to recover for recycle of a useful aqueous liquid, and obtain the desired nitrogen-containing products. According to the invention aqueous solutions are fractionated in an integrated system of multi-stage columns while an effective polymerization inhibiting amount of at least one member of a preselected class of p-phenylenediamine compounds is maintained therein.

9 Claims, 1 Drawing Sheet

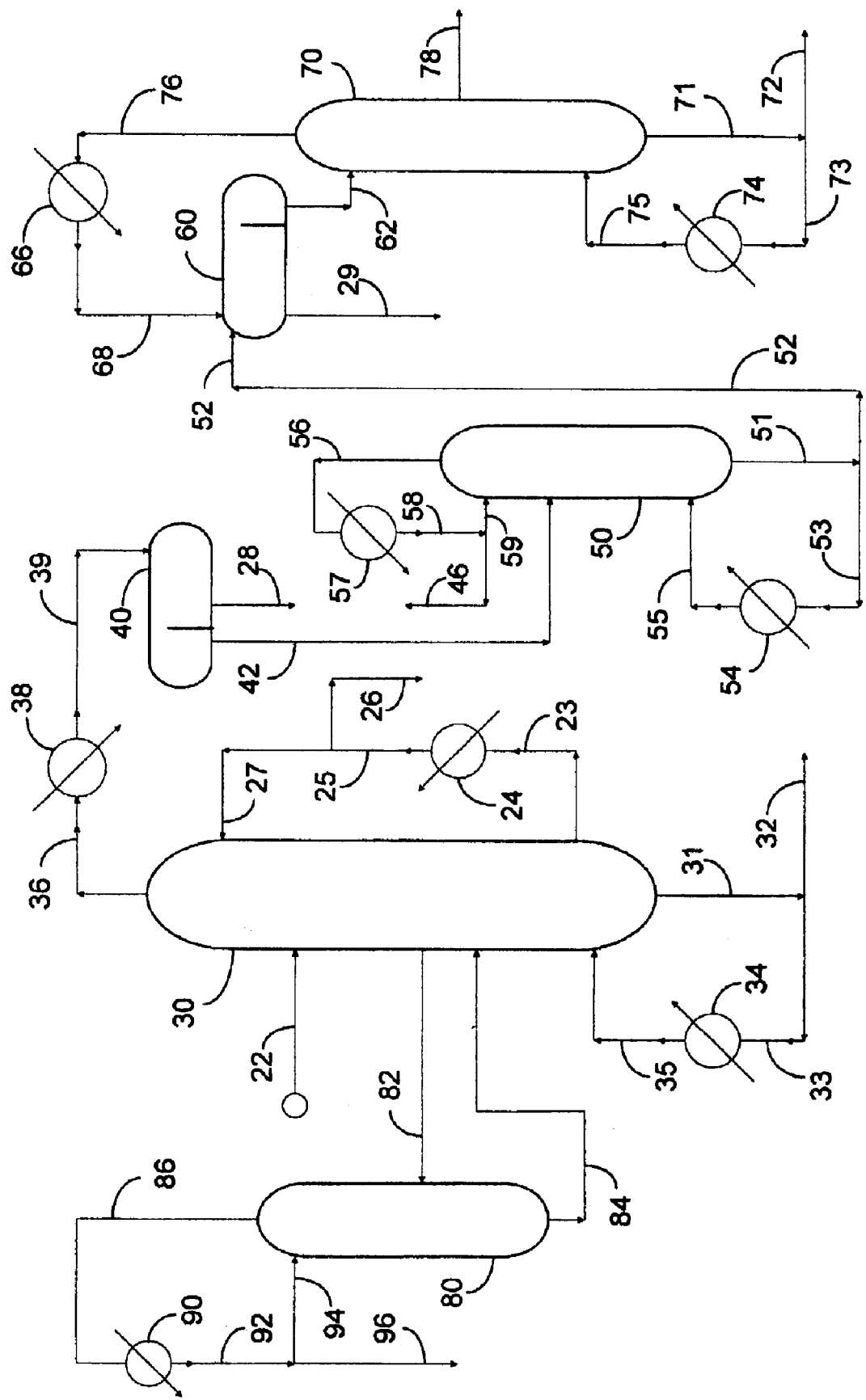

METHOD FOR INHIBITING POLYMERIZATION DURING THE RECOVERY AND PURIFICATION OF UNSATURATED MONONITRILES

FIELD OF THE INVENTION

The field of this invention relates to continuous processes for recovery and purification of organic values from hot gaseous mixtures which are obtained by catalytic ammoxidation of a light hydrocarbon compounds. More particularly, this invention relates to recovery and refining of valuable nitrogen-containing organic compounds formed by catalytic oxidation of least one feed compound selected from the group consisting of propane, propylene, isobutane and isobutylene in the presence of ammonia to produce a gaseous reactor effluent containing the corresponding unsaturated mononitrile. Processes of the invention include quenching the gaseous reactor effluent with an aqueous quench liquid; forming an aqueous solution comprising the corresponding unsaturated mononitrile, hydrogen cyanide and other organic co-products; and using an integrated sequence of distillations and phase separations to recover for recycle of a useful aqueous liquid, and obtain valuable nitrogen-containing organic compounds and hydrogen cyanide products. Beneficially, according to the invention aqueous solutions are fractionated in an integrated system of multi-stage columns while an effective polymerization inhibiting amount of at least one member of a preselected class of p-phenylenediamine compounds is maintained therein.

BACKGROUND OF THE INVENTION

As is well known, most of the commercial acrylonitrile is produced with the Sohio Process from propylene by heterogeneous catalytic ammoxidation of propylene in the vapor phase with ammonia, air and steam. For exmple see U.S. Pat. Nos. 3,222,422 in the name of L.A. Cohen; 3,278,642 and 3,346,520 both in the name of L. Lee; 3,442,981 in the name of O.L. Stafford, D.V. Wing and D.E. Stolsmark; and 3,509,238 in the name of N.E. Aubery and M.B. Jastrzebeski.

In a commercial acrylonitrile system utilizing this process, the reactor feeds are propylene, ammonia and compressed air. The propylene and ammonia are vaporized, then combined with the air and fed to a fluidized bed catalytic reactor. Precise ratios of the three feeds are maintained for optimum yield. The catalyst in the reactor vessel is in the form of particles, which are maintained in a turbulent fluid state by the velocity of gaseous flow through the bed.

Propylene, ammonia and oxygen mix together in the reactor and oxidation of propylene in the presence of ammonia takes place on the surface of the fluidized catalyst. A set of complex exothermic reactions takes place, thereby forming the following products: acrylonitrile, hydrogen cyanide, carbon dioxide, carbon monoxide, acetonitrile, acrolein, acrylic acid, water, other higher nitrites, aldehydes, ketones, acetic acid and a number of miscellaneous unknown organic compounds. Conversion of the three feeds is less than 100 percent, thus unreacted propylene, ammonia, oxygen and nitrogen are contained in the reactor effluent gas. The source of propylene typically contains a small amount of propane and some heavier hydrocarbon compounds which most of which are purged from the process unreacted. A portion of the heat of the exothermic reaction is removed by sets of steam coils which generate and superheat waste steam at approximately 600 psig for process uses such as heat input for 9distillations in the products recovery and purification section of the process. Reactor effluent gas passes through cyclones, which remove catalyst fines from the gas. The gas is then further cooled in a reactor effluent cooler, which is comprised of a shell and tube exchanger using boiler feedwater as the cooling source.

As the gas leaves the reactor effluent cooler, it then enters a quench column. The quench column cools the reactor effluent by contacting it with a recirculating water stream. Most of the water vapor and small amounts of organic vapors in the reactor effluent are condensed in the quench column. The quench column bottoms are cooled and circulated back to the quench column. The quench column can contain internal trays or packing to provide intimate contact of upflowing gas with downflowing water. Sulfuric acid is injected into the recirculating quench water to neutralize unreacted ammonia in the reactor effluent. The excess quench water is roughly equal to the amount of water produced by the reactor and is fed to the wastewater column where acrylonitrile and hydrogen cyanide are recovered. Wastewater column bottoms are cooled and neutralized, mixed with other plant waste streams, clarified and injected into the wastewater injection well. The quench column effluent gas is then directed to an absorber where chilled water is used to obtain an aqueous solution of acrylonitrile, hydrogen cyanide and other organics from the gas.

The aqueous solution from the absorber is fed to a recovery column where acrylonitrile and hydrogen cyanide are taken overhead. A portion of the bottoms from the recovery column is cooled and recycled to the absorption step. This recycle contains both inorganic and organic compounds in the form of monomers, oligomers, prepolymers, and polymers in various combinations. Acrylonitrile, hydrogen cyanide and optionally acetonitrile products are then purified using a series of distillations and phase separations. A first column (heads column) removes hydrogen cyanide, and at last column (acrylonitrile product column) takes a pure acrylonitrile monomer product from a side-draw near the top of the column. High-boiling organic compounds are rejected from the product column bottoms.

Acrylonitrile can polymerize in the quench column. More specifically, as the reactor effluent gas is passed through the quench column, a portion of the acrylonitrile contained in the gas polymerizes and is absorbed into the recirculating quench water. The amount of acrylonitrile that polymerizes in the quench column represents an undesirable net product loss for the acrylonitrile plant. For example, in an uninhibited quench column, between about 2 to 5 percent of the total acrylonitrile produced by the reactor is lost due to polymerization in the quench column.

Several methods are known to reduce losses of acrylonitrile by polymerization and other side reactions, which involve treating the recirculating quench water. For example see U.S. Pat. Nos. 3,691,226; 4,720,566; 5,869,730; 5,895, 822 and 6,238,574, which patents are incorporated herein by reference.

U.S. Pat. No. 4,720,566, in the name of John F. Martin, describes methods and compositions for inhibiting acrylonitrile polymerization in quench columns of systems producing acrylonitrile with a combination of (a) a hydroxylamine having two alkyl groups, and (b) a para-phenylenediamine with a substituent phenyl group or unsubstituted para-phenylenediamine.

Unfortunately, under operating conditions, acrylonitrile can also polymerize in the recovery and purification sections to from solid deposits which interfere with operation of equipment, contribute to an undesirable net production loss and reduction in production rates, and with time lead to costly shutdowns.

Such polymers, oligomers, and prepolymers, in various combinations, foul heat exchange surfaces of the heat exchangers used to maintain operating conditions for separation in the distillation columns and other process equipment. Fouled heat exchange surfaces reduce the coefficient of heat transfer thereby increasing the amount of heat transfer medium which must be used to realize the required amount of heating and/or cooling obtained on clean surfaces. Eventually, the heat exchanger must be manually cleaned with potential exposure of personnel to hazardous chemicals.

It is therefore a general object of the present invention to provide an improved process which overcomes the aforesaid problem of prior art methods for to recovery and refining of valuable nitrogen-containing organic compounds formed by catalytic oxidation of least one feed compound selected from the group consisting of propane, propylene, isobutane and isobutylene in the presence of ammonia.

Improved processes would utilize a preselected class of polymerization inhibiting compositions effective under operating conditions during fractional distillations of aqueous solutions comprising the unsaturated mononitrile products.

Advantageously, members of such a class of inhibiting compositions would be effectively separated by the fractional distillation of the purified products.

Other objects and advantages of the invention will become apparent upon reading the following detailed description and appended claims.

SUMMARY OF THE INVENTION

Economical processes are disclosed for recovery of valuable nitrogen-containing organic compounds formed by catalytic ammoxidation of propane, propylene, isobutane, and/or isobutylene with ammonia and a gaseous source of dioxygen and steam. Nitrogen-containing organic compounds produced in the catalytic oxidation reactions are recovered from product gaseous stream as a aqueous solution. The aqueous solution containing the unsaturated mononitrile is transferred to a recovery and purification section where the unsaturated mononitrile is recovered and purified in at least a first distillation column and at least one product distillation columns wherein high-boiling impurities are separated from the unsaturated mononitrile by distillation.

Under operating conditions, unsaturated mononitrile, e.g., acrylonitrile or methacrylonitrile, and other organic compounds present, can polymerize in the recovery and purification sections to from solid deposits which interfere with operation of equipment, contribute to an undesirable net production loss and reduction in production rates, and with time lead to costly shutdowns.

Processes of this invention comprise: (a) reacting at least one feed compound selected from the group consisting of propane, propylene, isobutane and isobutylene, with ammonia and a source of dioxygen in the presence of a catalyst a reactor to produce a reactor effluent containing the corresponding unsaturated mononitrile; (b) transferring the reactor effluent containing the unsaturated mononitrile to a quench/absorption section wherein the reactor effluent containing the unsaturated mononitrile is contacted with at least a first aqueous stream to cool the reactor effluent, and thereafter the cool effluent is contacted with at least a second aqueous stream in an absorption column to separate and recover the unsaturated mononitrile in an aqueous solution; (c) transferring the aqueous solution containing the unsaturated mononitrile to a recovery and purification section where the unsaturated mononitrile is recovered and purified in at least a first distillation column and a second distillation column; and (d) maintaining within one or more of the distillation columns an effective polymerization inhibiting amount of at least one phenylenediamine compound represented by the formula:

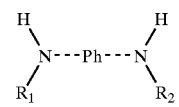

I wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group.

In a preferred class of phenylenediamine compounds the organic moieties ($R_1$ and $R_2$) are members of a group consisting of ethyl, propyl, butyl, phenyl, hexyl, heptyl, octyl nonyl and decyl hydrocarbon groups, particularly straight and branched-chain hydrocarbon groups. Advantageously, this class consists of N,N'-dialkyl-p-phenylenediamine compounds. More preferably at least one of the compounds is a member of a group consisting of N,N'-di-sec-propyl-p-phenylenediamine, N,N'-di-sec-butyl-p-phenylenediamine, N,N'-di-isobutyl-p-phenylenediamine, and N,N'-di-tert-butyl-p-phenylenediamine. Most preferably the p-phenylenediamine is N,N'-di-sec-butyl-p-phenylenediamine for best results.

In preferred embodiments of the invention, the effective polymerization inhibiting amount is no less than about 5 parts per million parts of unsaturated mononitrile present in the aqueous solution. Generally, the effective polymerization inhibiting amount is in a range upward from about 10 to about 10,000 parts per million parts of acrylonitrile in the aqueous solution. Preferably in a range from about 50 to about 1000 parts per million parts of acrylonitrile the aqueous solution. Most preferably in a range from about 75 to about 750 parts per million parts of acrylonitrile the aqueous solution.

Processes of the invention preferably include admixing of a liquid source of the phenylenediamine compound with an aqueous solution containing the unsaturated mononitrile which is being transferred into the first distillation column and/or one or more product distillation columns. Preferably the phenylenediamine compound is in the liquid state at conditions from ambient up to about 60° C.,however the liquid source of the phenylenediamine compound may also be a solution of the phenylenediamine compound in the unsaturated mononitrile, water, or a combination thereof.

In preferred embodiments of the invention, the unsaturated mononitrile is acrylonitrile or methacrylonitrile, and the feed compound is a corresponding olefin selected from the group consisting of propylene and isobutylene. In other preferred embodiments of the invention, the unsaturated mononitrile is acrylonitrile, and the feed compounds are members of a group consisting of propane and propylene.

One aspect of the invention provides a process for recovery of valuable nitrogen-containing organic compounds formed by catalytic ammoxidation of propane, propylene or isobutylene with ammonia and a gaseous source of dioxygen which process comprises: providing an aqueous solution comprising acrylonitrile or methacrylonitrile, hydrogen cyanide and other organic co-products; fractionating the aqueous solution as by distillation in at least a first multi-stage column and a second multi-stage column; and maintaining within the columns an effective polymerization inhibiting amount of at least one compound represented by the formula I, wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group. Advantageously, the effective polymerization inhibiting amount is in a range upward from about 50 to about 1000 parts per million parts of unsaturated mononitrile present in the aqueous solution.

An aspect of special significance is that the feed compounds are members of a group consisting of propane and propylene.

Another aspect of the invention provides a process for recovery of valuable nitrogen-containing organic compounds formed by catalytic ammoxidation of propylene and/or propane with ammonia and a gaseous source of dioxygen which process comprises: providing an aqueous solution comprising acrylonitrile, hydrogen cyanide and other organic co-products of an ammoxidation reaction of propylene and/or propane with ammonia and a gaseous source of dioxygen; fractionating the aqueous solution as by distillation in a multi-stage column to obtain a high boiling fraction comprising a major amount of the acrylonitrile in the aqueous solution and a low boiling fraction comprising a major amount of the hydrogen cyanide in the aqueous solution; and maintaining within the column an effective polymerization inhibiting amount of at least one phenylenediamine compound represented by the above formula I: wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group.

Yet another aspect of the invention provides a process for recovery of valuable nitrogen-containing organic compounds formed by catalytic ammoxidation of propylene or propane with ammonia and a gaseous source of dioxygen which process comprises: providing an aqueous solution comprising acrylonitrile and high-boiling organic compounds; fractionating the aqueous solution as by distillation in a multi-stage column to obtain a high boiling fraction comprising a high boiling fraction comprising essentially all the organic compounds boiling above about 100° C., a sidedraw product stream comprising at least 99 percent by weight of acrylonitrile, and a low boiling fraction substantially free of the high-boiling organic compounds; and maintaining within the column an effective polymerization inhibiting amount of at least one compound represented by the above formula I: wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group.

A preferred aspect of the invention provides a process for recovery of valuable nitrogen-containing organic compounds formed by catalytic ammoxidation of isobutylene or isobutane with ammonia and a gaseous source of dioxygen which process comprises: providing an aqueous solution comprising methacrylonitrile, hydrogen cyanide and other organic co-products of an ammoxidation reaction of isobutylene and/or isobutane with ammonia and a gaseous source of dioxygen; fractionating the aqueous solution as by distillation in a multi-stage column to obtain a high boiling fraction comprising a major amount of the methacrylonitrile in the aqueous solution and a low boiling fraction comprising a major amount of the hydrogen cyanide in the aqueous solution; and maintaining within the column an effective polymerization inhibiting amount of at least one compound represented by the above formula I: wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group.

Another preferred aspect of the invention provides a process for recovery of valuable nitrogen-containing organic compounds which process comprises: forming a gaseous reaction effluent by ammoxidation of propylene with ammonia and a gaseous source of dioxygen in the presence of a heterogeneous catalyst comprising cobalt; contacting the gaseous reaction effluent with an aqueous liquid to obtain an aqueous solution comprising acrylonitrile, hydrogen cyanide and other organic co-products; fractionating the aqueous solution as by distillation in a multi-stage column to obtain a high boiling fraction comprising a major amount of the acrylonitrile in the aqueous solution and a low boiling fraction comprising a major amount of the hydrogen cyanide in the aqueous solution; and maintaining within the column an effective polymerization inhibiting amount of at least one compound represented by the above formula I: wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group.

The total amount of p-phenylenediamine compounds of the preselected class used in the compositions and methods of the present invention as polymerization inhibitor is that amount which is sufficient of effect inhibition of polymerization of the unsaturated aliphatic nitrile product and will, of course, vary according to the particular conditions under which they are used. Where process stream are maintained at higher temperatures and/or longer durations, larger amunts are generaly required. Preferably, during one or more of the extractions, distillations, and phase separations for recovery and purification, the total amount of of p-phenylenediamine compounds of the preselected class is no less than about 5 parts per million parts of unsaturated aliphatic nitrile present in the aqueous solution. Typically, the effective polymerization inhibiting amount is in a range upward from about 10 to about 10,000 parts per million parts of unsaturated aliphatic nitrile e in the aqueous solution. More preferably in a range from about 50 to about 1000 parts per million parts of unsaturated aliphatic nitrile the aqueous solution. Most preferably in a range from about 75 to about 750 parts per million parts of unsaturated aliphatic nitrile the aqueous solution.

For a more complete understanding of the present invention, reference should now be made to the embodiments illustrated in greater detail in the accompanying drawing and described below by way of examples of the invention.

BRIEF DESCRIPTION OF THE FIGURE

The appended claims set forth those novel features which characterize the present invention. The present invention itself, as well as advantages thereof, may best be understood, however, by reference to the following brief description of preferred embodiments taken in conjunction with the annexed drawing, in which:

The FIGURE is a schematic diagram depicting a preferred method for operating the process of this invention in the continuous mode being arranged to provide an integrated sequence of extractions, distillations, and phase separations for recovery and purification, and to maintain suitable operating conditions in accordance with the present invention, thereby obtaining valuable nitrogen-containing organic compounds.

BRIEF DESCRIPTION OF THE INVENTION

Processes of this invention are particularly suitable for use in recovery and refining of an unsaturated aliphatic nitrile product, such as acrylonitrile or methacrylonitrile, from a gaseous mixture produced, generally, by gas-phase catalytic oxidation and/or thermal oxidation of olefin and ammonia with a source of dioxygen, typically comprising compressed air. The well known and most widely used commercial processes for production of acrylonitrile by ammoxidation of propylene with ammonia is the Sohio Process.

As is well known, performance of the oxidation catalysts is an important factor, perhaps the most significant factor, in the economics of this and other oxidation processes. Catalyst performance is measured by activity, i.e., conversion of reactants, selectivity, i.e. conversion of reactant to desired product, rate of production of desired product per unit of reactor volume per unit of time, and catalyst life, i.e. effective time on-stream before significant loss of activity or selectivity.

The practice of the process of the present invention is not dependent upon any specific ammoxidation fluid bed catalyst. Suitable catalysts which are more selective for the ammoxidation of propylene and isobutylene can be prepared from bismuth, cobalt, iron, nickel, tin salts, and molybdic, molybdic phosphoric, and molybdic silicic acids. Other components, such as tungsten, copper, tellurium, and arsenic oxides, have been incorporated to increase low temperature activity and productivity.

Factors upon which catalyst performance depends include composition, the methods of preparation, support, and calcination conditions. Other key properties include, In addition to chemical performance requirements, other key properties include surface area, porosity, density, pore size distribution, hardness, strength, and resistance to mechanical attrition.

Patents claiming specific catalysts and processes for their use in the manufacture of acrylonitrile and methacrylonitrile by the ammoxidation of propylene and isobutylene, respectively, include U.S. Pat. Nos. 2,481,826; 2,904,580; 3,044,966; 3,050,546; 3,197,419; 3,198,750; 3,200,084; 3,230,246, 3,248,340 and 3,352,764 which patents are incorporated herein by reference.

Feeds for the ammoxidation combine to contain a mixture of propylene, air, ammonia, and optionally an supplementary source of dioxygen. Beneficially, feed compositions range up to about 9 percent propylene on molar basis. Gaseous mixtures in the ammoxidation reactors are kept too low in oxygen to be flammable during normal operation. Reactor start-up and shutdown procedures are likewise designed to avoid flammable feed mixtures.

Effluent from the ammoxidation reactor is cooled in a quench tower with an acidified water stream by countercurrent contact. Gases from the quench tower are transferred into the bottom of an absorber where acrylonitrile, acetonitrile and other relatively soluble gases are absorbed. The non-absorbed gases are vented.

The stream from the bottom of the absorber, known as the rich water stream, is transferred into a recovery column where it is extractively distilled. The recovery column may be any suitable contacting means in which liquid and vapor are counter-currently contacted in a multiplicity of communicating zones or stages. The overhead vapors from the recovery column are enriched in acrylonitrile, other components being chiefly water and hydrogen cyanide, and contaminated with undesirable impurities such as nitrites, compounds which have characteristics of nitrites, and precursors thereof. The overhead vapors are condensed and collected in a decanter, the liquid undergoes liquid—liquid phase separation, the less dense layer being an organic phase, the denser lower layer being an aqueous phase. The organic phase being chiefly acrylonitrile contaminated with water and hydrogen cyanide, is withdrawn for further purification. The aqueous phase is refluxed to the upper section of the recovery column.

Embodiments of the present invention can include known treatments of process streams. For example, U.S. Pat. No. 3,442,771 disclosed a process for removal of trace impurities (e.g. nitrites, peroxides and precursors thereof) from unsaturated mononitriles (e.g. acrylonitrile) contaminated with water which process uses the addition of an alkaline solution to the partially condensed azeotrope of the unsaturated nitrile and water where the azeotrope has been obtained as an overhead stream obtained from an extractive distillation column, in particular, the recovery column. The effect of the alkaline solution is to extract the reaction product of the trace impurities into the aqueous phase of the azeotrope leaving the organic phase relatively impurity-free. The azeotrope is then transferred into a decanter where liquid—liquid phase separation occurs. The organic phase containing crude acrylonitrile is then removed for further purification while the aqueous phase containing the reaction products is recycled to the recovery column.

In a preferred embodiment of the present invention one or more of the aqueous recycle streams is treated with an acid to reduce the pH. Preferably, the acid may be a mineral acid such as sulfuric or an organic acid such as acetic, acrylic, formic or glycol, determined by cost considerations, availability, compatibility, metallurgy, etc.

Under operating conditions, acrylonitrile can polymerize in the recovery and purification sections to from solid deposits which interfere with operation of equipment, contribute to an undesirable net production loss and reduction in production rates, and with time lead to costly shutdowns.

Beneficially, in the practice of processes of the present invention, polymerization inhibitor is fed to each unit to maintain an effective polymerization inhibiting amount of at least one the preselected p-phenylenediamine compounds and thereby prevent polymer formation and resulting equipment failure.

BRIEF DESCRIPTION OF PREFERRED EMBODIMENTS OF THE INVENTION

While this invention is susceptible of embodiment in many different forms, this specification and accompanying drawing disclose only some specific forms as an example of the use of the invention. In particular, preferred embodiments of the invention which include ammoxidation of propylene with ammonia and a source of dioxygen, quenching the gaseous mixture from the ammoxidation with an aqueous quench liquid to obtain an aqueous solution comprising acrylonitrile, hydrogen cyanide, acetonitrile and other organic co-products, and an integrated sequence of distillations and phase separations to recover and purify the acrylonitrile product, recover hydrogen cyanide and, optionally, acetonitrile products are illustrated and/or described.

As embodied and broadly described herein, the process of the present invention comprises reacting an olefin selected from the group consisting of propylene and isobutylene, ammonia and oxygen in a reactor zone in the presence of a catalyst to produce a reactor effluent containing the corresponding unsaturated mononitrile (i.e. acrylonitrile of methacrylonitrile), transferring the reactor effluent containing the unsaturated mononitrile to a quench column wherein the reactor effluent containing the unsaturated mononitrile is contacted with at least a first aqueous stream to cool the reactor effluent, transferring the cooled reactor effluent containing the unsaturated mononitrile to an absorption column wherein the reactor effluent containing unsaturated mononitrile is contacted with at least a second aqueous stream to separate and remove the unsaturated mononitrile as a bottom stream from the absorption column, transferring the bottom stream containing the unsaturated mononitrile to a recovery and purification section where the unsaturated mononitrile is recovered and purified, and recycling at least one aqueous process stream to improve the efficiency of the process.

The invention is not intended to be limited to the embodiments so described, and the scope of the invention will be pointed out in the appended claims.

Apparatus of this invention is used with certain conventional components the details of which, although not fully illustrated or described, will be apparent to those having skill in the art and an understanding of the necessary function of such components. Examples of plant ancillaries not illustrated or described include; facilities for preparation and distribution of polymerization inhibitor and/or solutions thereof, steam ejector or vacuum pump systems to maintain the required operating pressures for distillations at mild conditions of temperature, collection and disposal systems for waste liquids, and emergency vent systems.

Preferably processes of this invention derive a suitable gaseous mixture from the air oxidation of an olefin selected from the group consisting of propylene and isobutylene over a solid, particulate catalyst in the presence of ammonia. A suitable sources of olefin can contain up to about 15 percent of the corresponding alkane, typically from about 2 to about 10 percent, and up to about 5 percent heavier hydrocarbon compounds, and preferably less than about 2 percent.

For best results the ammoxidation process is carried out in a fluid-bed reactor for best results. Because of the high olefin conversions obtained, a single pass system is typically satisfactory. Approximately stoichiometric quantities of propylene, ammonia, and dioxygen are introduced into a fluidized bed of catalytic particles. Suitable operating conditions include pressures in a range from about 3 to about 35 psig (20.7 to 241.4 kPa gage), more preferably from about 5 to about 25 psig (34.5 to 172.4 kPa gage). Generally, temperatures are in a range from about 700° to 1000° F. (371° to 538° C.), preferable in a range from about 750° to 950° F. (399° to 510° C.). Heat of reaction is is removed by generation of steam to control the temperature and generating steam at temperatures of from about 300° to about 500° C elevated pressure.

Advantageously, the oxidations are operated at the lowest temperature consistent with high conversion. Conversion increases with temperature; the selectivity generally decreases only with large increases in temperature. Catalyst life also decreases with increasing temperatures. Catalysts are designed to give high performance over a range of operating conditions permitting gradual increase of temperature over the operating life of the catalysts to maintain productivity and selectivity near the initial levels, thus compensating for gradual loss of catalyst activity.

Because commercial catalysts achieve high conversion of propylene to acrylonitrile, once-through operation of the ammoxidation reactor with a residence time of a few seconds is typical. Commercially recoverable quantities of acetonitrile and hydrocyanic acid are optional co-products.

Effluent from the ammoxidation reactor is cooled and is scrubbed with water in a counter-current, absorbing system from which off-gas, consisting chiefly of nitrogen, is vented. Organic products, primarily acrylonitrile, acetonitrile and HCN, are collected in water to give up to about 8 percent aqueous acrylonitrile and co-products, preferably from about 2.5 to about 7.5 percent, more preferably from about 3 to about 7 percent of acrylonitrile and co-products, for best results.

The aqueous solution of acrylonitrile and co-products is treated in an integrated system of distillation and phase separation steps by which organic products are recovered and at least acrylonitrile is refined. The aqueous solution is sent to the acrylonitrile recovery column, from which an overhead stream containing crude acrylonitrile and HCN is recovered. A liquid side stream from the column is fractionated in a small column to the remove acetonitrile as a co-product or, more typically, for disposal by incineration. Water is removed from the bottom of the acrylonitrile recovery column. Condensate from the overhead stream is separated, and the HCN removed in the overhead of the heads column. The acrylonitrile in the bottoms is further purified in the product column to obtain fiber-grade acrylonitrile.

More specifically with reference to the FIGURE, which is a schematic illustration of an integrated distillation means for obtaining valuable acrylonitrile product and hydrogen cyanide according to a preferred embodiment of the invention, where separation of organic compounds from the aqueous solution is illustrated as recovery column 30 and decantation drum 40; recovery of the hydrogen cyanide is illustrated as lights separation column 50; and purification of acrylonitrile product is illustrated as decantation drum 60 and product column 70.

Generally, during operation of the integrated processes for recovery and refining at least acrylonitrile from a gaseous mixture obtainable by catalytic ammoxidation of propylene and ammonia with dioxygen, an aqueous solution which contains the organic products of the ammoxidation is obtained by quenching the gaseous effluent from the ammoxidation reactor with an aqueous quench liquid.

The aqueous solution is fed from the quench system or intermediate storage (not shown) through conduit 22 and into the upper part of recovery column 30. A liquid stream is withdrawn from near the bottom of recovery column 30 through conduit 23, and cooled in exchanger 24. A suitable portion of the cooled liquid stream is dispersed into the upper part of recovery column 30 through conduit 25 and the balance of the stream is sent to an acetonitrile recovery and/or disposal (not shown). An aqueous stream from the bottom of recovery column 30 is recycled to the quench system through manifold 31 and conduit 32. As needed in order to maintain suitable conditions of separation in recovery column 30, liquid from the bottom thereof circulates through manifold 31 and conduit 33, reboiler 34 and into the column through conduit 35.

After disengagement from the top of recovery column 30, a stream of vapors flows into condenser 38 through conduit 36, and together with condensate into decantation drum 40 through conduit 39. The more-dense phase is withdrawn from decantation drum 40 through conduit 28 and sent back into recovery column 30 typically, combined with the aqueous feed solution. The less-dense phase is transferred from decantation drum 40 through conduit 42 and fed into lights separation column 50.

As needed in order to maintain suitable conditions of separation in separation column 50, liquid from the bottom thereof circulates through manifold 51 conduit 53, reboiler 54 and into the column through conduit 55. After disengagement from the top of lights separation column 50, a stream of vapors flows through conduit 56 and into condenser system 57. As needed for reflux, a stream of condensate is transferred into lights separation column 50, through manifold 58 and conduit 59. Condensate comprising hydrogen cyanide is sent to hydrogen cyanide storage tanks (not shown) through conduit 46.

During operation of the separation column in accordance with the invention, an effective polymerization inhibiting amount of a composition comprising at least one p-phenylenediamine represented by formula I, preferably a p-phenylenediamine selected from the group consisting of N,N'-di-sec-propyl-p-phenylenediamine, N,N'-di-sec-butyl-p-phenylenediamine, N,N'-di-isobutyl-p-phenylenediamine, and N,N'-di-tert-butyl-p-phenylenediamine, is maintained therein.

Generally, the effective polymerization inhibiting amount is no less than about 5 parts per million parts of unsaturated mononitrile present in the aqueous solution. In preferred embodiments of the invention, the effective polymerization inhibiting amount is in a range upward from about 10 to about 10,000 parts per million parts of acrylonitrile in the aqueous solution. More preferably, effective amounts are in a range from about 50 to about 1000 parts per million parts of acrylonitrile the aqueous solution. Most preferably, effective amounts are in a range from about 75 to about 750 parts per million parts of acrylonitrile the aqueous solution.

Liquid is withdrawn from the bottom of separation column 50 is transferred into decantation drum 60 through manifold 51 conduit 52. The more-dense phase is withdrawn from decantation drum 60 through conduit 29 and sent back into recovery column 30 typically, combined with the aqueous feed solution. The less-dense phase is transferred from decantation drum 60 through conduit 62 and fed into product column 70 near the top the column. Pure acrylonitrile monomer product is withdrawn from a side-draw through conduit 78 and sent to storage (not shown). From the bottom of product column 70, an aqueous stream comprising heavy organic compounds is sent through conduit 72 to a waste water disposal system (not shown). After disengagement from the top of product column 70, a stream of vapors flows into condenser 66 through conduit 76, and, together with condensate, into decantation drum 60 through conduit 68.

During operation of the product column and/or decantation in accordance with the invention, an effective polymerization inhibiting amount of a composition comprising at least one p-phenylenediamine represented by formula I, preferably a p-phenylenediamine selected from the group consisting of N,N'-di-sec-propyl-p-phenylenediamine, N,N'-di-sec-butyl-p-phenylenedi amine, N,N'-di-isobutyl-p-phenylenediamine, and N,N'-di-tert-butyl-p-phenylenediamine, is maintained therein.

Generally, in these operations the effective polymerization inhibiting amount is no less than about 5 parts per million parts of unsaturated mononitrile present in the aqueous solution. In preferred embodiments of the invention, the effective polymerization inhibiting amount is in a range upward from about 10 to about 10,000 parts per million parts of acrylonitrile in the aqueous solution. More preferably, effective amounts are in a range from about 50 to about 1000 parts per million parts of acrylonitrile the aqueous solution. Most preferably, effective amounts are in a range from about 75 to about 750 parts per million parts of acrylonitrile the aqueous solution.

A stream is withdrawn from a side-draw on recovery column 30 through conduit 82 and fed into fractionation column 80. A liquid stream from the bottom of fractionation column 80 is returned to recovery column 30 below the side-draw through conduit 84. After disengagement from the top of fractionation column 80, a stream of vapors flows through conduit 86 and into condenser 90 where condensate comprising acetonitrile is formed. A portion of the condensed phase is transferred into of fractionation column 80, as reflux through manifold 92 and conduit 94. Another portion of the condensed phase is transferred through conduit 96 into crude acetonitrile storage tanks and/or disposal (not shown).

Preferred embodiments of the invention recover an acrylonitrile product which contains at least 90 percent of the acrylonitrile contained in the aqueous solution, more preferably about 95 percent of the acrylonitrile contained in the aqueous solution is recovered as monomer-grade product.

EXAMPLES OF THE INVENTION

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

Equipment

An internally heated cell was used to screen polymerization inhibitors. A Hach 2100AN turbidimeter connected to a strip chart was used to detect solution turbidity. The acrylonitrile used was distilled prior to use. A constant temperature bath was used to circulate the hot water/ethylene glycol solution through the heated cell to maintain the desired temperature where the turbidity was monitored.

General Procedure

Antioxidants were used as received from the supplier. 2,2-Azo-bis-isobutyronitrile (AIBN) was the free radical source. The general method for testing involved preparing a mixture of freshly distilled acrylonitrile, an inhibitor and AIBN and subjecting this mixture to an elevated temperature while monitoring turbidity.

Examples 1–13

These examples demonstrate the use of N,N'-di-sec-butyl-p-phenylenediamine, identified below as DBPA inhibitor.

Example 1

A mixture of 18.94 grams of acrylonitrile and 0.00241 grams of DBPA inhibitor were placed in the hot tube and 0.0266 grams of AIBN was then added to the mixture. The mixture was heated to 65° C. and the turbidity was monitored. The onset of turbidity occurred after 228 minutes. The molar ratio of AIBN to DBPA inhibitor was 15

Example 2

Example 1 was repeated except that the molar ratio of AIBN to DBPA inhibitor was 22. The onset of turbidity occurred after 150 minutes.

Example 3

Example 1 was repeated except that the molar ratio of AIBN to DBPA inhibitor was 29. The onset of turbidity occurred after 128 minutes.

Comparative Examples A–C

These comparative examples are to illustrate the use of compounds which are hydroxy derivatives of benzene having an OH group is attached directly to a benzene ring, i.e., phenols, to inhibit polymerization.

Comparative Example A

A mixture of 18.97 grams of acrylonitrile and 0.00232 grams of hydroquinone (p-dihydroxybenzene, M.P. 170.3° C.,) were placed in the hot tube and 0.0554 grams of AIBN was then added to the mixture. The mixture was heated to 65° C. and the turbidity was monitored. The onset of turbidity occurred after 74 minutes. The molar ratio of AIBN to inhibitor was 16.

Comparative Example B

Comparative Example A was repeated except that the molar ratio of AIBN to inhibitor was 18. The onset of turbidity occurred after 56 minutes.

Comparative Example C

Comparative Example A was repeated except that the molar ratio of AIBN to inhibitor was 31. The onset of turbidity occurred after 20 minutes.

These data show that the time to onset of turbity, over range for the molar ratio of AIBN to inhibitor of 15 to 30, the use of N,N'-di-sec-butyl-p-phenylenediamine was 3 to 4⅔ times longer than using hydroquinone.

Comparative Example D

A mixture of 19.26 grams of acrylonitrile and 0.00087 grams of hydroquinone and 0.00106 grams of DBPA inhibitor were placed in the hot tube and 0.0500 grams of AIBN was then added to the mixture. The mixture was heated to 65° C. and the turbidity was monitored. The onset of turbidity occurred after 74 minutes. The molar ratio of AIBN to inhibitor was 24.

This comparative example shows that using a combination of hydroquinone (p-dihydroxybenzene) and the AIBN inhibitor of the invention (N,N'-di-sec-butyl-p-phenylenediamine) decreased the time to onset of turbity to about ½ of the time using AIBN alone.

Example 4

A mixture of 18.38 grams of acrylonitrile and 0.00241 grams of DBPA inhibitor and 0.01862 grams of glacial acetic acid were placed in the hot tube and 0.0492 grams of AIBN was then added to the mixture. The mixture was heated to 65° C. and the turbidity was monitored. The onset of turbidity occurred after 130 minutes. The molar ratio of AIBN to inhibitor was 27. Acetic acid can be used in the process to control pH and this example demonstrates that acetic acid does not adversely impact the performance of DBPA inhibitor.

Example 5

A mixture of 19.09 grams of acrylonitrile and 0.00244 grams of DBPA inhibitor and 0.00156 grams of acrylic acid were placed in the hot tube and 0.0515 grams of AIBN was then added to the mixture. The mixture was heated to 65° C. and the turbidity was monitored. The onset of turbidity occurred after 129 minutes. The molar ratio of AIBN to inhibitor was 28. Acrylic acid is a co-product that can be produced and this example demonstrates that acrylic acid does not adversely impact the performance of DBPA inhibitor.

Comparative Example E

This comparative example is to illustrate the use of an amine compound which has two benzene rings, i.e., diphenylamine, to inhibit polymerization. A mixture of 19.95 grams of acrylonitrile and 0.00184 grams of diphenylamine (M.P. 52° C.) were placed in the hot tube and 0.0363 grams of AIBN was then added to the mixture. The mixture was heated to 65° C. and the turbidity was monitored. The onset of turbidity occurred after 84 minutes. The molar ratio of AIBN to inhibitor was 20.

Comparative Examples F & G

These comparative examples are to illustrate the very poor results obtained in comparable use of compounds which are derivatives of hydroxyamine to inhibit polymerization.

Example F

A mixture of 20.46 grams of acrylonitrile and 0.00201 grams of N,N-diethylhydroxylamine were placed in the hot tube and 0.040 grams of AIBN was then added to the mixture. The mixture was heated to 65° C. and the turbidity was monitored. The onset of turbidity occurred after 10 minutes. The molar ratio of AIBN to inhibitor was 11.

Example G

Example 5 was repeated except that the molar ratio of AIBN to inhibitor was 4. The onset of turbidity occurred after 14 minutes.

For the purposes of the present invention, "fractional distillation" is defined as a method to separate a mixture of several volatile components of different boiling points; the mixture is distilled at the lowest boiling point, and the distillate is collected as one fraction until the temperature of the vapor rises showing that the composition of the vapor being distilled has changed: this vapor is collected as a separate fraction. "Fractionation" is defined as separation of a mixture in successive stages, each stage removing from the mixture some proportion of one of the substances as by distillation. Unless indicated otherwise, "column" is defined as an apparatus used widely for continuous separation of fluid (gaseous or liquid) components by vapor-liquid fractionation.

For the purposes of the present invention, "predominantly" is defined as more than about fifty per cent. "Substantially" is defined as occurring with sufficient frequency or being present in such proportions as to measurably affect macroscopic properties of an associated compound or system. Where the frequency or proportion for such impact is not clear substantially is to be regarded as about twenty per cent or more. The term "Essentially" is defined as absolutely except that small variations which have no more than a negligible effect on macroscopic qualities and final outcome are permitted, typically up to about one percent.

Examples have been presented and hypotheses advanced herein in order to better communicate certain facets of the invention. The scope of the invention is determined solely by the scope of the appended claims.

That which is claimed is:

1. A process for manufacturing an unsaturated mononitrile which process comprises:

reacting at least one feed compound selected from the group consisting of propane, propylene, isobutane and isobutylene, with ammonia and a source comprising dioxygen in the presence of a catalyst in a reactor to produce a reactor effluent containing the corresponding unsaturated mononitrile;

transferring the reactor effluent containing the unsaturated mononitrile to a quench/absorption section wherein the reactor effluent containing the unsaturated mononitrile is contacted with at least a first aqueous stream to cool the reactor effluent, and thereafter the cool effluent is contacted with at least a second aqueous stream in an absorption column to separate and recover the unsaturated mononitrile in an aqueous solution;

transferring the aqueous solution containing the unsaturated mononitrile to a recovery and purification section where the unsaturated mononitrile is recovered and purified in at least a first distillation column and a second distillation column; and maintaining within one or more of the distillation columns an effective polymerization inhibiting amount of at least one phenylenediamine compound represented by the formula:

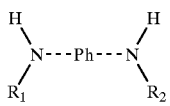

wherein Ph is a phenylene group, and $R_1$ and $R_2$ are the same or different and are hydroxyl free organic moieties having about 2 to about 10 carbon atoms with the proviso that neither $R_1$ nor $R_2$ is a phenyl group.

2. The process according to claim 1 wherein the effective polymerization inhibiting amount is no less than about 5 parts per million parts of unsaturated mononitrile present in the aqueous solution.

3. The process according to claim 2 which further comprises admixing a liquid source of the phenylenediamine compound with an aqueous solution containing the unsaturated mononitrile which is being transferred into the first distillation column and/or second distillation column.

4. The process according to claim 1 wherein the unsaturated mononitrile is acrylonitrile or methacrylonitrile, and the feed compound is a corresponding olefin selected from the group consisting of propylene and isobutylene.

5. The process according to claim 1 wherein the organic moieties $R_1$ and $R_2$ are members of a group consisting of ethyl, propyl, butyl, phenyl, hexyl, heptyl, octyl, nonyl and decyl straight and branched-chain hydrocarbon groups.

6. The process according to claim 1 wherein the phenylenediamine compound is selected from of a group consisting of N,N'-dialkyl-p-phenylenediamine compounds.

7. The process according to claim 1 wherein the unsaturated mononitrile is acrylonitrile, and the feed compounds are members of a group consisting of propane and propylene.

8. The process according to claim 7 wherein the phenylenediamine compound is selected from a group consisting of N,N'-di-sec-propyl-p-phenylenediamine, N,N'-di-sec-butyl-p-phenylenediamine, N,N'-di-isobutyl-p-phenylenediamine, and N,N'-di-tert-butyl-p-phenylenediamine.

9. The process according to claim 8 wherein the compound is N,N'-di-sec-butyl-p-phenylenediamine.

* * * * *